(12) United States Patent
Unger et al.

(10) Patent No.: US 10,499,954 B2
(45) Date of Patent: Dec. 10, 2019

(54) BONE ANCHOR WITH DEPLOYABLE PURCHASE ELEMENT

(71) Applicant: NUVASIVE, INC., San Diego, CA (US)

(72) Inventors: Jesse Unger, San Diego, CA (US); Robert German, San Diego, CA (US); Nicholas Didier, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 92 days.

(21) Appl. No.: 15/604,322

(22) Filed: May 24, 2017

(65) Prior Publication Data

US 2017/0258497 A1    Sep. 14, 2017

Related U.S. Application Data

(63) Continuation of application No. PCT/US2017/021763, filed on Mar. 10, 2017.

(60) Provisional application No. 62/306,201, filed on Mar. 10, 2016.

(51) Int. Cl.
*A61B 17/70* (2006.01)
*A61B 17/56* (2006.01)

(52) U.S. Cl.
CPC ...... *A61B 17/7032* (2013.01); *A61B 17/7047* (2013.01); *A61B 17/7056* (2013.01); *A61B 2017/564* (2013.01)

(58) Field of Classification Search
CPC ............ A61B 17/7056; A61B 17/7032; A61B 17/7047; A61B 17/707
See application file for complete search history.

(56) References Cited

U.S. PATENT DOCUMENTS

| 4,433,676 | A |   | 2/1984  | Bobechko |
|-----------|---|---|---------|----------|
| 4,641,636 | A |   | 2/1987  | Cotrel |
| 5,000,165 | A |   | 3/1991  | Watanabe |
| 5,024,213 | A |   | 6/1991  | Asher et al. |
| 5,176,678 | A |   | 1/1993  | Tsou |
| 5,246,442 | A |   | 9/1993  | Ashman et al. |
| 5,257,993 | A |   | 11/1993 | Asher et al. |
| 5,263,954 | A |   | 11/1993 | Schlapfer et al. |
| 5,267,999 | A |   | 12/1993 | Olerud |
| 5,374,267 | A | * | 12/1994 | Siegal ............... A61B 17/7049 606/250 |
| 5,403,314 | A |   | 4/1995  | Currier |
| 5,454,812 | A |   | 10/1995 | Lin |
| 5,476,464 | A |   | 12/1995 | Metz-Stavenhagen et al. |
| 5,507,747 | A | * | 4/1996  | Yuan ................. A61B 17/7043 24/514 |
| 5,584,832 | A |   | 12/1996 | Schlapfer |
| 5,630,816 | A |   | 5/1997  | Kambin |
| 5,632,744 | A |   | 5/1997  | Campbell, Jr. |

(Continued)

FOREIGN PATENT DOCUMENTS

FR    2642642    8/1990

*Primary Examiner* — Jacqueline T Johanas

(57) ABSTRACT

A bone anchor is provided for connecting a rod to a bone structure, the bone anchor having a rod housing configured to accommodate the rod; a cavity distal to the rod housing dimensioned to accommodate the bone structure; and a deployable purchase element capable of assuming a deployed position in which the purchase element protrudes into the cavity, and capable of assuming a non-deployed position in which the purchase element does not substantially protrude into the cavity.

21 Claims, 3 Drawing Sheets

(56) References Cited

U.S. PATENT DOCUMENTS

| | | | |
|---|---|---|---|
| 5,688,273 A | 11/1997 | Errico et al. | |
| 5,702,452 A | 12/1997 | Argenson et al. | |
| 5,810,818 A | 9/1998 | Errico et al. | |
| 5,944,720 A | 8/1999 | Lipton | |
| 6,352,537 B1* | 3/2002 | Strnad | A61B 17/7007 606/276 |
| 6,475,218 B2 | 11/2002 | Gournay et al. | |
| 6,656,180 B2* | 12/2003 | Stahurski | A61B 17/7056 606/276 |
| 6,740,089 B2 | 5/2004 | Haider | |
| 6,932,817 B2* | 8/2005 | Baynham | A61B 17/7032 606/330 |
| 7,338,490 B2* | 3/2008 | Ogilvie | A61B 17/7053 606/276 |
| 8,075,597 B2* | 12/2011 | Stahurski | A61B 17/7032 606/260 |
| 8,828,058 B2 | 9/2014 | Elsebaie et al. | |
| 9,314,285 B2 | 4/2016 | Reisberg | |
| 9,468,470 B2* | 10/2016 | Legallois | A61B 17/7032 |
| 2003/0045876 A1* | 3/2003 | Stahurski | A61B 17/7056 606/276 |
| 2003/0130659 A1* | 7/2003 | Haider | A61B 17/7032 606/302 |
| 2003/0187437 A1 | 10/2003 | Ginsburg | |
| 2006/0015099 A1 | 1/2006 | Cannon et al. | |
| 2007/0016189 A1* | 1/2007 | Lake | A61B 17/7044 606/250 |
| 2007/0072459 A1* | 3/2007 | Stahurski | A61B 17/7032 439/135 |
| 2007/0161990 A1 | 7/2007 | Hillyard et al. | |
| 2007/0276384 A1 | 11/2007 | Spratt | |
| 2008/0086131 A1* | 4/2008 | Daly | A61B 17/7032 606/264 |
| 2009/0306722 A1* | 12/2009 | Lewis | A61B 17/7056 606/276 |
| 2012/0215268 A1* | 8/2012 | Stahurski | A61B 17/7032 606/86 R |
| 2013/0231704 A1* | 9/2013 | Larroque-Lahitette | A61B 17/7056 606/277 |
| 2014/0277155 A1* | 9/2014 | Barrus | A61B 17/7056 606/276 |
| 2014/0277163 A1* | 9/2014 | Kretzer | A61B 17/7049 606/278 |
| 2014/0330319 A1* | 11/2014 | Khatchadourian | A61B 17/7014 606/279 |
| 2014/0343612 A1 | 11/2014 | Rezach et al. | |
| 2015/0112391 A1* | 4/2015 | Legallois | A61B 17/7032 606/276 |
| 2016/0015430 A1 | 1/2016 | Butterman | |
| 2016/0058478 A1* | 3/2016 | Agarwal | A61B 17/7032 606/270 |
| 2016/0151095 A1* | 6/2016 | Harper | A61B 17/7043 606/279 |
| 2016/0183981 A1 | 6/2016 | Schlaepfer et al. | |
| 2017/0181772 A1* | 6/2017 | Buttermann | A61B 17/7032 |
| 2017/0258497 A1* | 9/2017 | Unger | A61B 17/7032 |
| 2018/0132909 A1* | 5/2018 | Hackathorn, II | A61B 17/7065 |

\* cited by examiner

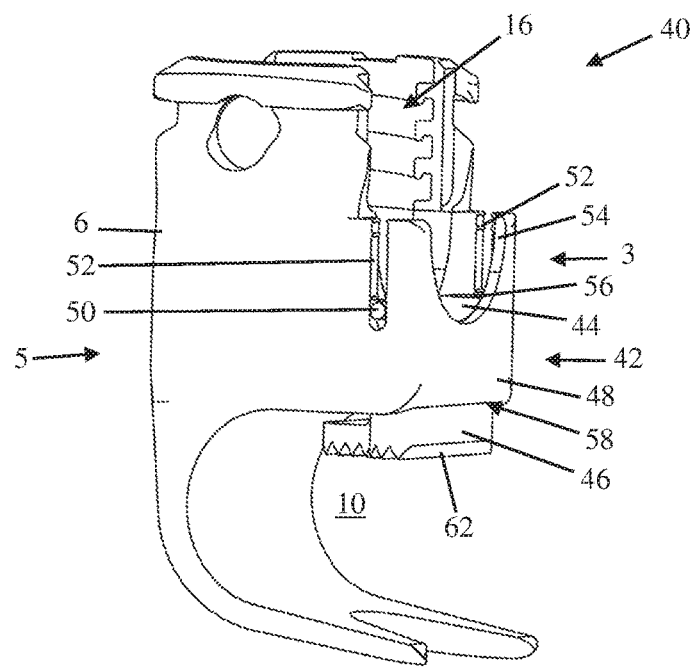
Fig. 8
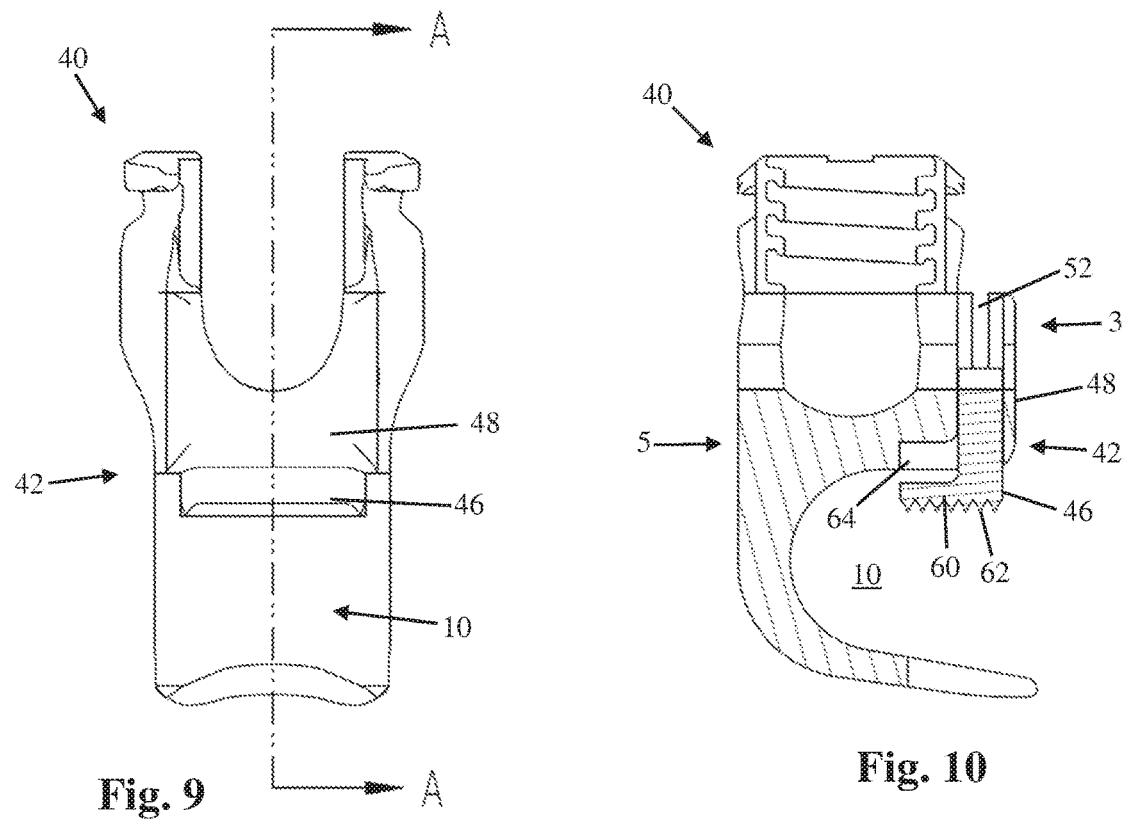
Fig. 9
Fig. 10

BONE ANCHOR WITH DEPLOYABLE PURCHASE ELEMENT

CROSS-REFERENCE TO RELATED APPLICATIONS

This application is a continuation of international patent application PCT/US17/21763, filed 10 Mar. 2017 (pending). International patent application PCT/US17/21763 cites the priority of U.S. patent application No. 62/306,201, filed on 10 Mar. 2016. All of the foregoing applications are incorporated by reference herein in their entireties.

BACKGROUND

Field

The present disclosure relates generally to medical devices, and specifically to surgical instruments and methods for performing spinal procedures.

Background

The spine is formed of a column of vertebra that extends between the cranium and pelvis. The three major sections of the spine are known as the cervical, thoracic and lumbar regions. There are 7 cervical vertebrae (C1-C7), 12 thoracic vertebrae (T1-T12), and 5 lumbar vertebrae (L1-L5), with each of the 24 vertebrae being separated from each other by an intervertebral disc. A series of about 9 fused vertebrae extend from the lumbar region of the spine and make up the sacral and coccygeal regions of the vertebral column. The natural curvature of the spine includes a combination of lordosis and kyphosis. Specifically, the cervical and lumbar portions of the spine exhibit a natural lordotic curvature, meaning that they are set in a curve that is anteriorly convex (and posteriorly concave). The thoracic portion of the spine has a naturally kyphotic curvature, meaning that it is set in a curve that is anteriorly concave (and posteriorly convex).

The main functions of the spine are to provide skeletal support and protect the spinal cord. Even slight disruptions to either the intervertebral discs or vertebrae can result in serious discomfort as well as compression of nerve fibers either within the spinal cord or extending from the spinal cord. If a disruption to the spine becomes severe enough, severe pain, disability and damage to a nerve or part of the spinal cord may occur and can result in partial to total loss of bodily functions (e.g., walking, talking, breathing, etc.). Therefore, it is of great interest and concern to be able to both correct and prevent any ailments of the spine.

Fixation systems are often surgically implanted to stabilize or immobilize a portion of the spine. They are generally utilized during spinal fusion procedures to immobilize the applicable vertebrae until bone growth occurs to effect the fusion and/or to correct vertebral alignment issues. Fixation systems often use a combination of rods, plates, pedicle screws, and bone hooks to attach a fixation construct to the affected vertebrae. The configuration required for each procedure and patient varies due to the ailment being treated, the specific method of treatment (e.g. surgical approach, etc.) and the patient's specific anatomical characteristics. One of the most common methods for achieving the desired immobilization is through the application of bone anchors (pedicle screws or hooks) that are then connected by rigid rods locked to each bone anchor. Pedicle screws, when used, are most often introduced into the pedicles associated with the respective vertebra to be fixed. Hooks, likewise, are attached with the pedicles associated with the respective vertebra to be fixed. Hook implants are used in order to provide alternative fixation to pedicle screws. Traditional hook implants are often placed in a caudal orientation at the upper instrumented vertebrae. In addition, hooks may be implemented when a pedicle is too small for a pedicle screw. Pedicle screws/hooks generally include an anchor component and a rod-housing component (or "tulip") that is coupled to the anchor component.

Traditional hooks rely upon caudal trajectory to maintain purchase on the vertebral body. As a result, this often requires the surgeon to violate and/or reset the superior facet joint. Alternatively, hook/claw constructs may be implemented by the surgeon to achieve enhanced purchase when compared to a single hook. The hook/claw construct involves placing two hooks, one facing caudal and the other cephalad, on opposing sides of the vertebral body. However, this once again requires the surgeon to violate the superior facet joint. Finally, hook with screw implants may be implemented to increase the purchase of a hook to the vertebral bone. The hook with screw may be placed in either the caudal or cephalad orientations depending on the surgical goals of the doctor. However, multiple steps are needed to implant the hook with screw, and often the screw must be inserted before the rod placement is normalized.

SUMMARY

The present disclosure describes a bone anchor, including methods of use thereof, useful for anchoring a spinal rod to a bone structure. Various embodiments of the bone anchor allow the bone anchor to be applied to different areas of the bone in different orientations, and through multiple surgical trajectories. This creates the possibility of using novel and unorthodox approaches that are impossible using conventional bone anchors. For example, rather than placing the bone anchor in a traditional caudal orientation, the bone anchor may be placed in a cephalad orientation.

In a first aspect, a bone anchor for connecting a rod to a bone structure is provided, the bone anchor comprising: a rod housing configured to accommodate the rod; a cavity distal to the rod housing dimensioned to accommodate the bone structure; and a deployable purchase element capable of assuming a deployed position in which the purchase element protrudes into the cavity, and capable of assuming a non-deployed position in which the purchase element does not substantially protrude into the cavity.

In a second aspect, a method of anchoring a spinal rod to a bone structure in a subject is provided, the method comprising: placing the bone structure within a cavity of a bone anchor; placing the spinal rod within a rod channel of the bone anchor; reducing the spinal rod in the rod channel; protruding a deployable purchase element into the cavity and in contact with the bone structure, such that movement between the deployable purchase element and the bone is restricted.

In a third aspect a spinal fixation system is provided, comprising the bone anchor above, a spinal rod fastened within the rod housing, and second bone anchor comprising a second rod housing, wherein the spinal rod is fastened within the second rod housing.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 8. A perspective view of an alternative embodiment of the bone anchor.

FIG. 9. A front plan view of the embodiment of the bone anchor shown in FIG. 8.

FIG. 10. A cross-sectional side view of the embodiment of the bone anchor shown in FIGS. 8 and 9.

DETAILED DESCRIPTION

Figure 1:
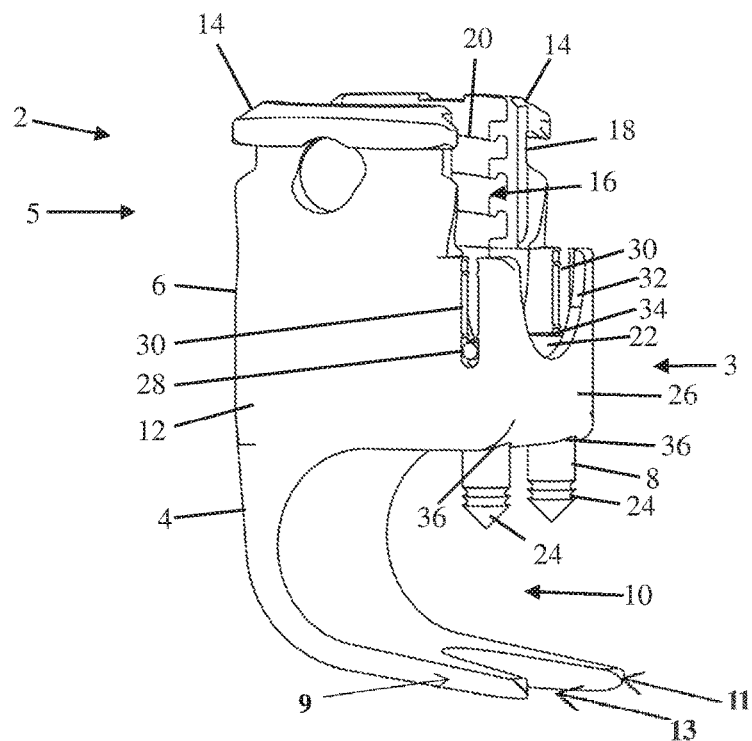
FIG. 1. A perspective view of an embodiment of the bone anchor.

Illustrative embodiments of a bone anchor are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The bone anchor disclosed herein boasts a variety of inventive features and components that warrant patent protection, both individually and in combination.

A bone anchor 2 for connecting a rod 38 to a bone structure is provided, the bone anchor 2 comprising: a rod housing 6 configured to accommodate the rod 38; a cavity 10 distal to the rod housing 6 dimensioned to accommodate the bone structure; and a deployable purchase element 8 capable of assuming a deployed position in which the purchase element 8 protrudes into the cavity 10, and capable of assuming a non-deployed position in which the purchase element 8 does not substantially protrude into the cavity 10. When the cavity 10 is positioned around the bone structure, the deployable purchase element 8 clamps the bone structure against part of the anchor 2 that defines the cavity 10 (such as a hook member 4, as shown in the illustrated embodiments). Some embodiments of the purchase element 8 penetrate the bone when deployed, securely holding the bone structure in place within the cavity 10. Such embodiments will comprise a penetrator 70 on the surface of the purchase element 8 that contacts the bone structure. Penetrators 70 can take many forms, such as a spike or a barbed spike. Multiple penetrators 70 may be present on the purchase element 8. The purchase element 8 may also comprise a surface that provides high contact pressure between the purchase element 8 and the bone without penetrating the bone, by decreasing the contact area between the purchase element 8 and the bone structure while maintaining constant force.

The bone structure is positioned within the cavity 10, which must be dimensioned to accommodate it. Various such dimensions are known in the art to accommodate various suitable bone structures. In specific embodiments, the cavity 10 may be dimensioned to accommodate a vertebral structure, such as a spinous process, a lamina, a pedicle, a superior articular process, an inferior articular process, and a rib. The cavity's dimensions may be varied according to the dimensions of the subject; for example, the cavity may be dimensioned to accommodate a bone structure of an adult, an adolescent, a child, or an infant.

Some embodiments of the bone anchor 2 are configured to cause the purchase element 8 to reposition from the non-deployed position and the deployed position when the rod 38 is seated in the rod housing 6. This allows the cavity 10 to be placed over the bone structure while the rod 38 is not seated, permitting the relative positions of the bone anchor 2, rod 38, and bone structure to be adjusted. Once the bone anchor 2, rod 38, and bone structure are in position, the rod 38 is reduced into the rod housing 6, causing the purchase element 8 to deploy and attach to the bone structure. As reduction immobilizes the rod 38 relative to the bone anchor 2, all three structures are then mutually immobile. In some embodiments this is accomplished when the purchase element 8 is caused to protrude into the rod channel 16 in the non-deployed position, but does not substantially protrude into the rod channel 16 in the deployed position. In such embodiments the rod 38 contacts the purchase element 8 when it is reduced into the rod channel 16 (or otherwise exerts force on the purchase element 8 with a vector toward the bone structure), and pushes into contact with the bone structure. The purchase element 8 may occupy a channel running from the rod channel 16 to the cavity 10, allowing it to protrude into either alternatively.

Two specific embodiments of the bone anchor 2 are shown in the accompanying drawings.

Figure 2:
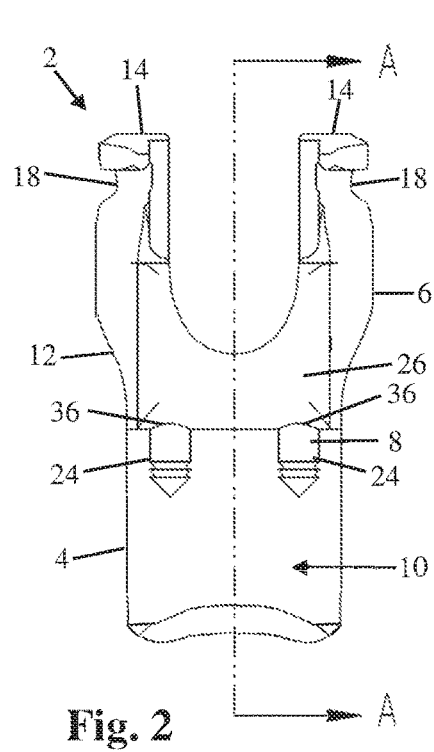
FIG. 2. A front plan view of the embodiment of the bone anchor shown in FIG. 1.
Figure 3:
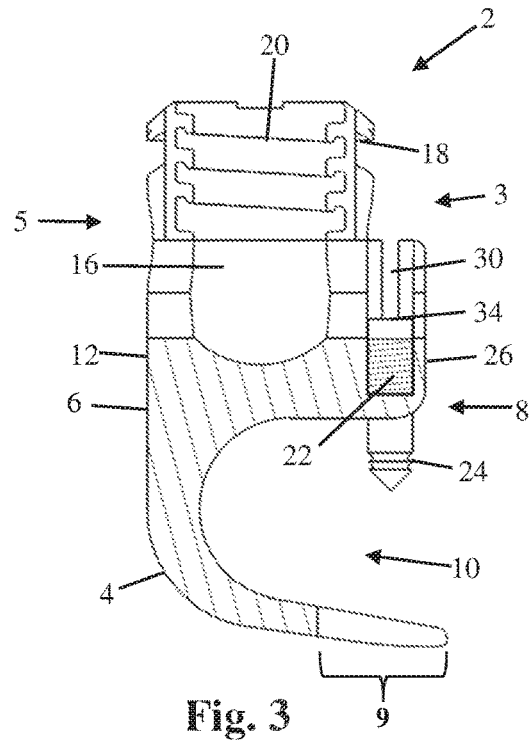
FIG. 3. A cross-sectional side view of the embodiment of the bone anchor shown in FIGS. 1 and 2.

FIGS. 1-3 illustrate an example of a bone anchor 2 according to a first embodiment. The bone anchor 2 has a front side 3, a back side 5, a hook member 4, a rod-housing 6, and a deployable purchase element 8. The hook member 4 extends distally from the back side 5 of the base of the rod housing 6 and then curves back toward the front side 3 forming a cavity 10 configured to receive at least a portion of a bony structure. The hook member 4 has a distal portion 9 formed by two prongs 11 with a groove 13 therebetween.

The housing 6 includes a base 12 and a pair of upstanding arms 14 extending from the base parallel to a longitudinal axis L of the base. Slots separating the upstanding arms 14 define a rod channel 16 passing through the rod housing 6. The arms 14 include tooling attachment features 18 for coupling the rod housing 6 to various tools useful during implantation of the bone anchor 2 and associated fixation construct (e.g. inserters, reducers, etc.) and locking cap engagement features 20 that cooperate with a locking cap (not shown) to capture and lock a rod 38 in the rod channel 16.

The deployable purchase element 8 is positioned on the front side 3 of the rod housing 6. By way of example, the deployable purchase element 8 includes a base 22 and one or more purchase members 24 extending distally from the base 22. The base 22 is slideably contained within a purchase element housing 26 positioned on the front 3 of the rod housing 6 and includes a pair of lateral pins 28 that track within longitudinal slots 30 formed within either side of the purchase element housing 26. The pins 28 ensure that the purchase element 8 deploys in a relatively straight-line fashion. The purchase element housing 26 further includes a generally U-shaped cutaway 32 on the front side 3 that is configured to receive the rod 38 and forms an extension of the rod channel 16 through the purchase element housing 26. The base 22 of the purchase element 8 includes a top surface 34 that interfaces with the rod 38 during deployment. The purchase members 24 extend from the bottom of the base 22 through a pair of apertures 36 formed in the purchase element housing 26. The deployable purchase element 8 may include any component that is capable of being passively moved from a first, open position in which the cavity 10 is unencumbered to a second, deployed position in which one or more purchase members 24 extend into the cavity 10 (and therefore into or onto bone). The purchase members 24 of the present example comprise a pair of spikes, however the purchase members 24 may comprise any structure capable of gaining purchase in bone, including but not limited to spikes, staple, clamp, and knurled surface, and the like.

Figure 4:
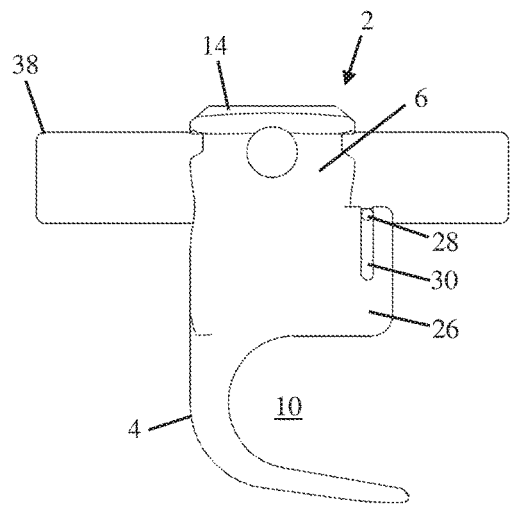
FIG. 4. A side plan view of the embodiment of the bone anchor shown in FIG. 1, in which a spinal rod is present in the rod channel, but has not been reduced.
Figure 5:
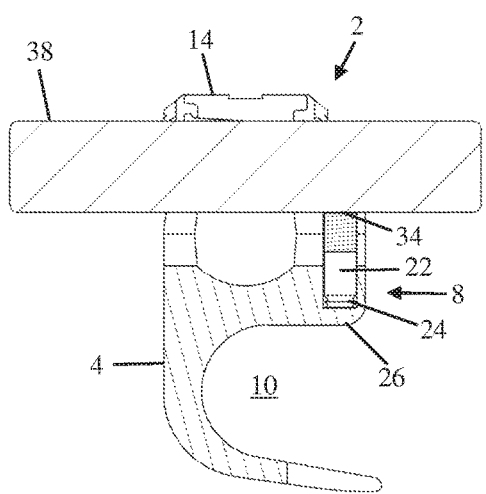
FIG. 5. A cross-sectional side view of the embodiment of the bone anchor shown in FIG. 4, showing that the purchase element is in its non-deployed position.

FIGS. 4-5 illustrate the bone anchor 2 in a first, open position, with the rod 38 positioned between upstanding arms 14 of the bone anchor 2. In the open position, the deployable purchase element 8 is biased within the purchase element housing 26 (e.g., by a spring-loaded bias, spot weld, frictional engagement, etc.) such that the purchase members 24 are fully contained within the housing 26 and therefore not extending into the cavity 10. The user can then position the bone anchor 2 in a desired location by inserting bony structure into the cavity 10. When the bone anchor 2 is in a desired position, the rod 38 is introduced into the rod channel 16, as depicted in FIGS. 4-5. At this point, the user may introduce additional bone anchors 2 on additional bony structures. When the user is ready to lock the construct in place, the rod 38 is reduced into the rod housing 6 in a normal fashion.

Figure 6:
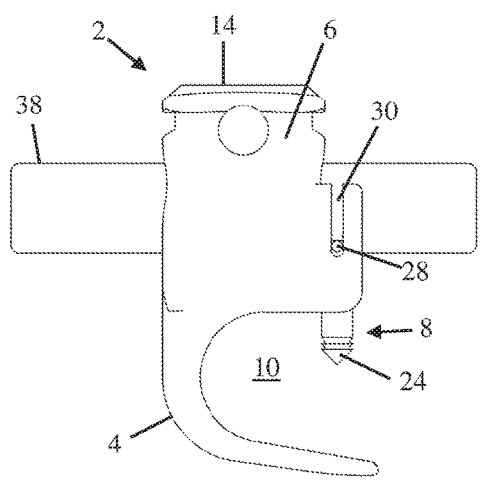
FIG. 6. A side plan view of the embodiment of the bone anchor shown in FIG. 1, in which a spinal rod is present in the rod channel, and has been fully reduced.
Figure 7:
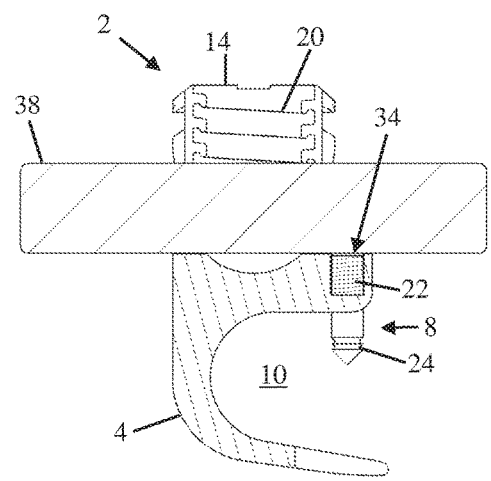
FIG. 7. A cross-sectional side view of the embodiment of the bone anchor shown in FIG. 6, showing that the purchase element is in its deployed position.

FIGS. 6-7 illustrate the bone anchor 2 in a second, deployed position, with the rod 38 reduced within the rod housing 6. As the user reduces the rod 38 in a usual manner, the rod 38 contacts the top surface 34 of the purchase element base 22. The reduction of the rod 38 then causes the purchase element base 22 to translate distally within the purchase element housing 26, which in turn forces the purchase members 24 into the cavity 10. Since the cavity 10 is occupied by bony structure, the purchase members 24 are urged into the bony structure. Once the rod 38 is fully reduced, a locking cap (not shown) is engaged with the locking cap engagement feature 20 of the rod housing 6 to secure the rod 38 within the rod channel 16. This in turn prevents the deployable purchase element 8 from retracting out of the bone due to the continuous blockage by the rod 38. Thus, the deployable purchase element 8 has a passive deployment mechanism and is self-locking.

FIGS. 8-10 illustrate an example of a bone anchor 40 having a deployable purchase element 42 according to a second embodiment. The bone anchor 40 is identical to the bone anchor 2 described above with the exception of the deployable purchase element 42 and relevant structure. Therefore, in the interest of clarity, like elements (in particular those related to the hook element 4 and rod housing 6) will be described with the same reference numerals as previously used.

The deployable purchase element 42 is positioned on the front side 3 of the rod housing 6. By way of example, the deployable purchase element 42 includes a base 44 and one or more purchase members 46 extending distally from the base 44. The base 44 is slideably contained within a purchase element housing 48 positioned on the front 3 of the rod housing 6 and includes a pair of lateral pins 50 that track within longitudinal slots 52 formed within either side of the purchase element housing 48. The pins 50 ensure that the purchase element 42 deploys in a relatively straight-line fashion when the rod 38 is reduced in the rod channel 16. The lateral pin 50 is positioned to be depressed by the rod 38 when the rod 38 is seated in the rod channel 16, and to exert force with a vector toward the bone structure on the purchase element 42 to cause the purchase element 42 to protrude into the cavity 10. The purchase element housing 48 further includes a generally U-shaped cutaway 54 on the front side 3 that is configured to receive the rod 38 and forms an extension of the rod channel 16 through the purchase element housing 48. The base 44 of the purchase element 42 includes a top surface 56 that interfaces with the rod 38 during deployment. The purchase member 46 extends from the bottom of the base 44 through an aperture 58 formed in the purchase element housing 48. The deployable purchase element 42 may include any component that is capable of being passively moved from a first, open position in which the cavity 10 is unencumbered to a second, deployed position in which one or more purchase members 46 extend into the cavity 10 (and therefore into or onto bone). The purchase member 46 of the present example comprises a clamp, however the purchase members 46 may comprise any structure capable of gaining purchase in bone, including but not limited to spikes, staple, clamp, and knurled surface, and the like. The purchase member 46 includes a foot portion 60 having a roughened bottom surface 62 configured to engage bony structure. The foot portion 60 extends laterally from the base 44 toward the back side 5 such that the foot portion 60, when deployed, extends back into the cavity 10. A recess 64 is formed in the bottom of the purchase element housing 48 to receive the foot portion 60 when the deployable purchase element 42 is in the open position.

The various examples of the bone anchor (2, 40) described herein have several advantages over the prior art devices. The passive fixation feature allows the bone anchor (2, 40) to be applied to different areas of the bone (e.g. seldom-used areas) in different orientations through unique surgical trajectories. For example, rather than placing a hook-type bone anchor 2 in a traditional caudal orientation, the bone anchor 2 may be placed in a cephalad orientation. This allows the surgeon to preserve the superior facet joint and create a more natural transition between the rigid surgical construct and the native anatomy, thus possibly reducing the incidence of proximal junction kyphosis. The coupled locking mechanism (rod 38 blocking the deployable purchase element 8 from retracting out of the bone) allows the rod 38/anchor 2 connection to be normalized prior to engaging the purchase element (by reducing the rod 38). This feature creates a safer, more balanced connection and further achieves this in a single step.

Any of the bone anchors (2, 40) described above may be incorporated into a spinal fixation system. The system may further comprise a spinal rod 38 fastened within the rod housing 6, and second bone anchor 66 comprising a second rod housing 68, wherein the spinal rod 38 is fastened within the second rod housing 68. Additional bone anchors may be present in multilevel systems for fixing the relative positions of three or more vertebrae, connected by either a single rod or multiple rods. The system may further comprise other components, such as inserters, reducers, locking caps, locking cap drivers, compression tools, distractors, retractors, and other such components of spinal fixation systems as are known in the art.

Any of the components of the bone anchors and systems described above may be wholly or partially constructed from a non-absorbable, biocompatible material. Specific examples of such materials include titanium, alloys of titanium, steel, stainless steel, aluminum oxide, calcium oxide, calcium phosphate, hydroxyapatite, zirconium oxide, and polymers such as polypropylene.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 and related laws or otherwise to provide organizational queues. These headings shall not limit or characterize the invention(s) set forth herein.

The following is claimed:

1. A bone anchor for connecting a rod to a bone structure, the bone anchor comprising a front, a back, opposing sides, a proximal end, and a distal end, the bone anchor further comprising:
    a rod housing configured to accommodate the rod;
    a hook member extending distally from the rod housing and curving forward, the hook member comprising a distal portion formed by two prongs with a groove therebetween;
    a cavity distal to the rod housing and dimensioned to accommodate the bone structure, the cavity bordered by the rod housing and the hook member;
    a purchase element housing positioned at the front of the bone anchor, wherein the purchase element housing is positioned above and in longitudinal alignment with the distal portion of the hook member; and
    a deployable purchase element movably received in the purchase element housing, the purchase element adapted to assume a retracted position in which the purchase element is retracted from the cavity, and adapted to assume a deployed position in which the purchase element is advanced into the cavity, wherein the purchase element comprises two purchase members, each purchase member comprising a distal tip, wherein each purchase member is adapted to be advanced toward and away from one of the prongs of the hook member.

2. The bone anchor of claim 1, wherein the rod housing comprises a pair of upright arm members defining a rod channel dimensioned to accommodate the rod.

3. The anchor of claim 2, wherein each of the upright arm members has a locking cap engagement feature.

4. The anchor of claim 3, wherein the locking cap engagement feature is an internal screw thread.

5. The anchor of claim 3, wherein the locking cap engagement feature includes a plurality of parallel grooves.

6. The bone anchor of claim 1, wherein the purchase element is configured to reposition from the retracted position to the deployed position when the rod is seated in the rod housing.

7. The bone anchor of claim 6, wherein the rod housing comprises a rod channel, and wherein the purchase element protrudes into the rod channel when in the retracted position, but is retracted from the rod channel when in the deployed position.

8. The bone anchor of claim 1, comprising a tool attachment feature on the rod housing.

9. The bone anchor of claim 1, wherein the purchase element translates longitudinally when repositioning between the retracted position and the deployed position.

10. The bone anchor of claim 1, wherein the purchase element comprises a base, wherein the base is slidably received in the purchase element housing.

11. The bone anchor of claim 10, wherein the base includes a pair of lateral pins that are received within longitudinal slots formed within two opposing sides of the purchase element housing.

12. The bone anchor of claim 11, wherein the pins are configured to ensure that the deployable purchase element deploys in a straight-line fashion.

13. The bone anchor of claim 1, wherein each distal tip comprises a bone penetrator adapted to penetrate bone structure.

14. A bone anchor for connecting a rod to a bone structure, the bone anchor comprising a front, a back, opposing sides, a proximal end, and a distal end, the bone anchor further comprising:
    a rod housing configured to accommodate the rod;
    a hook member extending distally from the rod housing and curving forward;
    a cavity distal to the rod housing and dimensioned to accommodate the bone structure, the cavity bordered by the rod housing and the hook member;
    a purchase element housing positioned at the front of the bone anchor; and
    a deployable purchase element movably received in the purchase element housing, the purchase element adapted to assume a retracted position in which the purchase element is retracted from the cavity, and adapted to assume a deployed position in which the purchase element is advanced into the cavity, wherein the purchase element comprises a base and a foot portion, the foot portion adapted to engage against bone structure, wherein the base is slidably received in the purchase element housing, wherein the foot portion extends laterally from the base toward the back of the bone anchor, wherein the purchase element housing comprises a recess adapted to receive the foot portion when the purchase element is in the retracted position.

15. The bone anchor of claim 14, wherein the deployable purchase element comprises a plurality of ridges at a distal end of the foot portion.

16. The bone anchor of claim 14, wherein the hook member comprises a distal portion formed by two prongs with a groove therebetween.

17. The bone anchor of claim 16, wherein the hook member distal portion is positioned directly below the purchase element housing.

18. The bone anchor of claim 14, wherein the purchase element is configured to reposition from the retracted position to the deployed position when the rod is seated in the rod housing.

19. The bone anchor of claim 18, wherein the rod housing comprises a rod channel, and wherein the purchase element protrudes into the rod channel when in the retracted position, but is retracted from the rod channel when in the deployed position.

20. The bone anchor of claim 14, comprising a tool attachment feature on the rod housing.

21. The bone anchor of claim 14, wherein the deployable purchase element translates longitudinally when repositioning between the retracted position and the deployed position.

\* \* \* \* \*